(12) United States Patent
Chang et al.

(10) Patent No.: US 7,312,369 B2
(45) Date of Patent: Dec. 25, 2007

(54) ATTRITION RESISTANT MOLECULAR SIEVE CATALYST, METHOD OF MAKING AND PROCESS FOR USING

(75) Inventors: Yun-Feng Chang, Houston, TX (US); Stephen N. Vaughn, Kingwood, TX (US); Kenneth R. Clem, Humble, TX (US); Luc R. Martens, Meise (BE); Alistair D. Westwood, Kingwood, TX (US); Jeffery W. Sprinkle, Baytown, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 703 days.

(21) Appl. No.: 10/833,483

(22) Filed: Apr. 28, 2004

(65) Prior Publication Data

US 2005/0245780 A1  Nov. 3, 2005

(51) Int. Cl.
*C07C 1/20* (2006.01)
(52) U.S. Cl. .................. 585/639; 585/638; 585/640

(58) Field of Classification Search ............... 585/639, 585/640, 638
See application file for complete search history.

(56) References Cited

U.S. PATENT DOCUMENTS

| 4,764,269 A | 8/1988 | Edwards et al. |
| 6,153,552 A | 11/2000 | Wachter et al. |
| 2003/0018228 A1 | 1/2003 | Vaughn et al. ............. 585/500 |

FOREIGN PATENT DOCUMENTS

| WO | WO 99/21651 | 5/1999 |
| WO | WO 02/05952 | 1/2002 |
| WO | WO 03/000412 | 1/2003 |
| WO | WO 2004/060559 | 7/2004 |

*Primary Examiner*—Tam M. Nguyen

(57) ABSTRACT

This invention provides an attrition resistant metalloaluminophosphate molecular sieve catalyst composition, methods of making the catalyst composition and processes for using the catalyst composition. The metalloaluminophosphate molecular sieve catalyst composition is highly attrition resistant in dried as well as fully calcined forms.

12 Claims, No Drawings

US 7,312,369 B2

ATTRITION RESISTANT MOLECULAR SIEVE CATALYST, METHOD OF MAKING AND PROCESS FOR USING

FIELD OF THE INVENTION

This invention concerns attrition resistant molecular sieve catalyst, as well as methods of making the catalyst and processes for using the catalyst. In particular, this invention concerns methods of making attrition resistant metalloaluminophosphate, particularly silicoaluminophosphate, molecular sieve catalyst (e.g., formulated molecular sieve catalyst), including methods of making the formulated catalyst and processes for using the formulated catalyst.

BACKGROUND OF THE INVENTION

Molecular sieve crystals are generally microporous structures composed of either crystalline aluminosilicate, belonging to a class of materials known as zeolites, or crystalline aluminophosphates, or crystalline metalloaluminophosphates such as silicoaluminophosphates. The crystals are conventionally made by hydrothermal crystallization from a reaction mixture comprising reactive sources of silicon and/or aluminum and/or phosphorous containing compounds, usually in the presence of one or several organic amine or quaternary ammonium salts.

Molecular sieve catalysts are compositions made of molecular sieve crystal particles bound together to form a formulated catalyst material. The formulated molecular sieve catalyst composition typically includes other components such as binders, fillers such as clay, and optionally other catalytically active agents such as rare earth metal oxides, transition metal oxides, or noble metal components.

Conventional methods of making molecular sieve catalysts include mixing together molecular sieve and binder, as well as other optional components such as fillers and other catalytic components. The mixture is typically stirred in solution to form a slurry, and the slurry is dried to form molecular sieve catalyst particles. Following drying, the particles are calcined to harden, as well as to activate, the catalyst.

U.S. Pat. No. 4,764,269 (Edwards) discloses conventional methods of making and using SAPO-37 molecular sieve catalyst that can be used in catalytic cracking operations. The catalyst was found to be adversely affected by moisture, but the crystalline structure and activity of the molecular sieve component was preserved by including a stabilizing amount of the organic template compound used in the manufacture of the molecular sieve within the pore structure thereof until such time as the catalyst was thermally activated during use.

Metalloaluminophosphate molecular sieves, such as the SAPO-37 molecular sieve described by Edwards, have a variety of uses. A desirable characteristic for many of the metalloaluminophosphate molecular sieves, regardless of the process of use, is that the finished or formulated catalyst be attrition resistant, which can refer to hardness as well as ability to absorb shock, since the catalyst will typically have to endure severe stress in commercial scale processes.

For example, WO 99/21651 describes a method for making molecular sieve catalyst that is considered relatively hard. The method includes the steps of mixing together a molecular sieve and an alumina sol, the alumina sol being made in solution and maintained at a pH of 2 to 10. The mixture is then spray dried and calcined. The calcined product is reported to be relatively hard, i.e., attrition resistant.

U.S. Pat. No. 6,153,552 describes another method for making molecular sieve catalyst. The catalyst is made by mixing together a silicon containing oxide sol as a binder material and a molecular sieve material. The pH of the mixture is adjusted prior to spray drying. Following spray drying, the catalyst material is calcined to form a finished catalyst product, which is reported to be relatively hard, i.e., attrition resistant.

Attrition resistance continues to be a desirable characteristic in molecular sieve catalysts. As new process systems are developed, the ability of the catalyst to endure the stress of the process system is particularly important so as to increase the effective life of the catalyst in the reaction process. If the catalyst is not properly attrition resistant, it is likely to break apart at an early stage, meaning that the catalyst could only be effectively used for a relatively short period of time. Therefore, obtaining molecular sieve catalysts that have a high degree of attrition resistance are still sought.

SUMMARY OF THE INVENTION

This invention provides molecular sieve catalyst, particularly metalloaluminophosphate molecular sieve catalyst, that is highly attrition resistant. Also provided are preferred methods of making the catalyst and preferred methods of using the catalyst.

According to one aspect of the invention, a metalloaluminophosphate molecular sieve is provided, which comprises molecular sieve crystals, clay and binder. In one embodiment, the catalyst has a core clay to alumina ratio of from 2.2:1 to 2.6:1. Preferably, the catalyst composition has a core clay to alumina ratio of from 2.3:1 to 2.5:1.

In another embodiment, the catalyst has a surface clay to alumina ratio of from 1.7:1 to 3.1:1. Preferably, the catalyst composition has a surface clay to alumina ratio of from 1.8:1 to 3:1, more preferably from 1.9:1 to 2.9:1, and most preferably from 2:1 to 2.8:1.

In yet another embodiment, the catalyst has an attrition rate index of not greater than 0.5 wt %/hr. Preferably, the catalyst composition has an attrition resistance index of not greater than 0.4 wt %/hr, more preferably not greater than 0.3 wt %/hr.

In another embodiment of the invention, the catalyst composition has an apparent bulk density of at least 0.83 g/cc. Preferably, the catalyst composition has an apparent bulk density of at least 0.84 g/cc, more preferably at least 0.85 g/cc and most preferably at least 0.86 g/cc.

According to one embodiment of the invention, the metalloaluminophosphate molecular sieve crystals are selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, metal containing molecular sieves thereof, and mixtures thereof. Preferably, the clay is a natural or synthetic clay. A preferred binder is an inorganic oxide sol of alumina or silica.

The catalyst composition is in dried form. In one embodiment, the dried catalyst is a spray dried catalyst composition. In another embodiment, the catalyst composition is a calcined catalyst composition.

The invention further provides a method of making an attrition resistant metalloaluminophosphate molecular sieve catalyst composition. In general, the method involves mixing together metalloaluminophosphate molecular sieve crystals, clay and binder at a breakage energy effective to break apart agglomerates and aggregates and achieving binding among sieve, binder, and matrix. The mixture is then dried to produce a dried metalloaluminophosphate molecular sieve catalyst composition. In one embodiment, the mixture is dried by spray drying. In another embodiment, spray dried metalloaluminophosphate molecular sieve catalyst composition is calcined to form a calcined metalloaluminophosphate molecular sieve catalyst.

In one embodiment of the method of the invention, the breakage energy is at least $10^{-5}$ cal cm$^{-2}$. Preferably, the breakage energy is at least $5 \times 10^{-5}$ cal cm$^{-2}$, more preferably the breakage energy is at least $10^{-4}$ cal cm$^{-2}$.

In another embodiment of the invention, the breakage energy is not greater than $10^{-1}$ cal cm$^{-2}$. Preferably, the breakage energy is not greater than $6 \times 10^{-2}$ cal cm$^{-2}$, more preferably not greater than $5 \times 10^{-2}$ cal cm$^{-2}$.

In another embodiment of the invention, the metalloaluminophosphate molecular sieve crystals, clay and binder are mixed together to form a mixture having a viscosity of at least 500 cP measured at 10 RPM using a Brookfield viscometer. In one embodiment, the mixture is aged prior to drying. Preferably, the mixture has a solids content of at least 40 wt %, based on total weight of the mixture. In another embodiment, it is preferred that the slurry has a solids content of not greater than 60 wt %.

In another embodiment, the metalloaluminophosphate molecular sieve crystals, clay and binder are mixed together at a binder to molecular sieve weight ratio of at least 0.20:1. In still another embodiment, the metalloaluminophosphate molecular sieve crystals, clay and binder are mixed together at a binder content of at least 5 wt %, based on total weight of the mixture, excluding liquid.

The invention further provides a process for making an olefin product from an oxygenate. In one embodiment, the process includes introducing a metalloaluminophosphate molecular sieve catalyst composition comprising metalloaluminophosphate molecular sieve crystals, clay and binder into a reaction system. The catalyst composition is then contacted with an oxygenate in the reaction system to form the olefin product.

In another embodiment, the invention provides a process for making olefin product, which includes a step of mixing together metalloaluminophosphate molecular sieve crystals, clay and binder at a breakage energy effective to break apart agglomerates and aggregates. The mixture is dried to produce a dried metalloaluminophosphate molecular sieve catalyst composition having a low attrition resistance index. The catalyst, in one embodiment, is then calcined to form a calcined metalloaluminophosphate molecular sieve catalyst, which also has a low attrition resistance index. The calcined catalyst is then contacted with oxygenate to form olefin product.

DETAILED DESCRIPTION OF THE INVENTION

I. General Description

This invention provides an attrition resistant metalloaluminophosphate molecular sieve catalyst composition, methods of making the catalyst composition and processes for using the catalyst composition. The metalloaluminophosphate molecular sieve catalyst composition is highly attrition resistant in dried as well as calcined forms.

According to this invention, attrition resistant refers to the ability to resist breaking apart as a result of physical impact. Since molecular sieve catalysts are often used in fluidized bed reaction systems or riser type reaction systems, the ability of such catalysts to avoid physical damage within the reaction systems is important. The catalyst of this invention is particularly attrition resistant. Attrition resistance, however, does not necessarily mean that the catalyst is hard, although hardness is a desirable characteristic. Attrition resistance can also be obtained through such characteristics as a catalyst's ability to absorb shock from impact as the catalyst is circulated through the reaction system. In some sense, the ability of the catalyst to absorb shock is similar to the ability of a ball to bounce off a hard surface with deforming the ball.

The catalyst of this invention exhibits high attrition resistance as a result of having a core composition that is substantially the same structure as its external surface. This means that the catalyst is substantially uniform in composition from the core region to the external surface of the catalyst. If the surface of the catalyst is substantially different from that of the core region, then there will be a tendency for the catalyst to break down or break apart as a result of physical stress. Thus, a relatively non-uniform catalyst structure results in a catalyst composition having reduced attrition resistance.

A preferred way of measuring surface composition is to measure the clay to alumina ratio at the surface of the catalyst. This can be accomplished using energy dispersive spectroscopy (EDS).

In this invention, EDS was performed using a Hitachi S-4300 scanning electron microscope equipped with a 30 mm$^2$ PGT Prism energy dispersive X-ray spectrometer. The following microscope and collection parameters were used: accelerating voltage=6 kV; objective aperture=1 (100 μm); $C_2$ spot size=5; working distance=15 mm; sample-detector distance≈25 mm; collection time=100 s; detector resolution=10 eV/channel; and a detector dead time≈10-20%. Under these collection conditions, the sampling depth for P Kα, Si Kα, Al Kα and O Kα X-rays is between≈2.2-2.5 μm (i.e., the maximum escape depth for X-rays) for a formulated catalyst sample having a bulk density of approximately 0.5 g/cm$^3$. This escape depth can be calculated using the Anderson-Hasler X-ray range equation [1], which requires the average density (0.5 g/cm$^3$ formulated catalyst) of the sample and the incident accelerating voltage (6 kV).

$$R_{X-Ray} = \frac{0.064(E_0^{1.68} - E_C^{1.68})}{\rho} \qquad [1]$$

In equation [1], $E_0$ is the incident accelerating voltage, $E_c$ is the characteristic X-ray energy and $\rho$ is the sample density.

Particles>50 μm in diameter were randomly selected to determine surface clay to alumina ratio. A 6×6 μm box was positioned on the crown of the particle and the beam rastered for 100 s across the 36 μm$^2$ region to collect the EDS spectrum. Typically, a total of 20 particles was analyzed for each sample.

In order to quantify the composition of EDS spectra from the 20 particles from each sample, standard spectra were collected from each of the individual components (molecular sieve, binder and clay). Using microscope settings and collection conditions indicated above, 20 individual spectra were collected from each reference material. A single reference spectra was generated from the 20 individual spectra by summing the 20 spectra and then dividing by 20 to from an average spectrum for the reference material.

A software package (IDL) was used to fit the entire spectra (0-6 keV) of each of the primary catalyst components (molecular sieve, binder and clay) against the 20 individual spectra that were collected from the 20 individual formulated catalyst particles. This allowed the relative concentrations of each of the three primary components in each particle to be determined. The fitting routine output as fractional components the relative contributions of the three reference spectra to the spectra collected from the particles.

In order to determine the degree of uniformity between the surface composition and the core composition of the catalyst, the clay to alumina ratio at the surface of the catalyst and at the core is compared. The clay to alumina ratio at the core region of the catalyst is determined by crushing a sample of the catalyst to form a bulk composition and using EDS to determine the clay to alumina ratio of the bulk composition in the same manner as for the surface samples.

Fractional amounts of crushed catalyst can be compared with known fractional components to develop a correction factor. For example, the deviation between measured and known catalyst components allowed for a X-ray absorption correction factor to be developed which was then applied to all of the spectra collected from the surface of the 20 particles analyzed per sample. This absorption corrected value of the original fractional components was then calculated and averaged for the 20 particles. The ratio of the average value measured from 20 particles provided the final clay/alumina ratio.

The catalyst of this invention is characterized by being highly uniform in composition, as well as attrition resistant. These characteristics are exhibited in all dried forms of the fully formulated catalyst composition, including spray dried forms and calcined forms. The advantage is that the catalyst does not have to be completely calcined to be considered attrition resistant, which is particularly advantageous with regards to shipping or storage. For example, the catalyst can be dried but not so extensively to remove template material from the catalyst. Leaving in the template material will provide increased protection to avoid damage of the catalyst activity as a result of contact with moisture. Even low levels of moisture (i.e., water) contacting internal catalyst sites can cause significant decreases in catalytic activity.

II. Catalyst Composition Components

A. Overall Composition

The catalyst of this invention is a metalloaluminophosphate molecular sieve catalyst composition, which comprises metalloaluminophosphate molecular sieve crystals, clay and binder. Such a combination is generally referred to as a formulated catalyst. In one aspect, the formulated catalyst composition is characterized by being highly resistant to attrition.

B. Molecular Sieve Crystal Component

The metalloaluminophosphate molecular sieve component can be represented by the empirical formula, on an anhydrous basis:

$mR:(M_xAl_yP_z)O_2$ wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIB and Lanthanide's of the Periodic Table of Elements, preferably M is selected from one of the group consisting of Si, Ge, Co, Cr, Cu, Fe, Ga, Ge, Mg, Mn, Ni, Sn, Ti, Zn, Zr and mixtures thereof. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Examples of metalloaluminophosphate molecular sieves which can be used in this invention are described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO.sub.4), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759, 919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605, 492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO_2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other metalloaluminophosphate molecular sieves include those described in EP-0 888 187 B1 (microporous crystalline metallophosphates, SAPO_4 (UIO-6)), U.S. Pat. No. 6,004,898 (molecular sieve and an alkaline earth metal), PCT WO 01/62382 published Aug. 30, 2001 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

Most preferably, the metalloaluminophosphate molecular sieve crystals present in the molecular sieve catalyst composition are selected from the group consisting of silicoaluminophosphate (SAPO) molecular sieves, aluminophosphate molecular sieves and metal substituted forms thereof. Non-limiting examples of SAPO and AlPO molecular sieves that may be present in the molecular sieve catalyst of the invention include molecular sieves selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, metal containing molecular sieves thereof, and mixtures thereof. The more preferred molecular sieves include molecular sieves selected from the group consisting of SAPO-18, SAPO-34, SAPO-35, SAPO-44, SAPO-56, AlPO-18 AlPO-34, metal containing molecular sieves thereof, and mixtures thereof; even more preferably molecular sieves selected from the group consisting of SAPO-18, SAPO-34, AlPO-34, AlPO-18, metal containing molecular sieves thereof, and mixtures thereof; and most preferably molecular sieves selected from the group consisting of SAPO-34, AlPO-18, metal containing molecular sieves thereof, and mixtures thereof.

As used herein, the term mixture is synonymous with combination and is considered a composition of matter having two or more components in varying proportions, regardless of their physical state. With regard to the molecular sieve crystal components of the catalyst, the term further encompasses physical mixtures of crystalline and amorphous components, as well as intergrowths of at least two different molecular sieve structures, such as for example those described in PCT Publication No. WO 98/15496.

In one embodiment, the molecular sieve crystal is an intergrowth material having two or more distinct phases of crystalline structures within one molecular sieve composition. In another embodiment, the molecular sieve crystal comprises at least one intergrown phase of AEI and CHA framework-types. For example, SAPO-18, AlPO-18 and RUW-18 have an AEI framework-type, and SAPO-34 has a CHA framework-type. In a further embodiment, the molecular sieve crystal comprises a mixture of intergrown material and non-intergrown material.

C. Clay Component

The clay component of the catalyst of this invention can be a natural or synthetic clay. Naturally occurring clays or modified natural occurring clays, e.g., partially dried or dehydrated, milled or micronized, or chemically treated are preferred. Such naturally occurring clays include clays from the kaolinite group, the mica group, the smectite group, and the chlorite group. Examples of kaolinite group clays include kaolinite, dickite and halloysite. Examples of the mica group clays include muscovite, illite, glauconite and biotite. Examples of the smectite group include montmorillonite and vermiculite. Examples of the chlorite group include penninite, clinochlore, ripidolite and chamosite.

Mixed layer clays can also be used. These clays are made of a regular or random stacking of layers composed of members of one or more groups of clay minerals. Chlorite may be seen as a regular alternation of mica and brucite layers. Random mixed layering of three layer clays is common, with examples being mixed layer mica/smectite and chlorite/vermiculite. In regular mixed layer structures such as chlorite, the basal spacing is a combination of that of the individual layers. In random mixed layering there is a non-integral series of reflections from the basal planes. This is shown as a composite reflection intermediate in position between those of the individual layers, or as a spreading of the reflection. Thus, when a significant amount of smectite is interlayered with mica in a random manner, the mica peak will not be sharp, but will be spread towards the lower angle smectite reflection. The amount of spreading depends on the amount of mixed layering that exists.

D. Binder Component

Binders that are used in this invention are materials that act like glue, binding together the molecular sieve crystals and other materials, to form a formulated molecular sieve catalyst composition. Non-limiting examples of binders that can be used in this invention include various types of inorganic oxide sols such as an inorganic oxide sol of alumina or silica, and in particular, aluminum chlorohydrate, hydrated aluminas, silicas, and/or other inorganic oxide sols.

E. Catalyst Composition Characteristics

One characteristic of the formulated catalyst composition of this invention is that it is substantially uniform in composition. The degree of uniformity from a core region of the catalyst to an external surface is preferably assessed by comparing the clay to alumina ratio of the catalyst at the core region and at the surface. A high degree of uniformity means that there are insubstantial differences between the clay to alumina ratio at the core and at the surface.

In one embodiment, the catalyst composition has a core clay to alumina ratio of from 2.2:1 to 2.6:1. Preferably, the catalyst composition has a core clay to alumina ratio of from 2.3:1 to 2.5:1.

In another embodiment, the catalyst composition has a surface clay to alumina ratio of from 1.7:1 to 3.1:1. Preferably, wherein the catalyst composition has a surface clay to alumina ratio of from 1.8:1 to 3:1, more preferably from 1.9:1 to 2.9:1, and most preferably from 2:1 to 2.8:1.

Another characteristic of the catalyst of this invention is that it is highly attrition resistant, as measured by the Attrition Rate Index (ARI) method. The ARI is used over other measurement methods, since many other methods are not sufficient to measure very highly attrition resistant molecular sieve catalysts such as those made according to this invention.

The ARI methodology is similar to the conventional Davison Index method. The smaller the ARI is, the more resistant to attrition the catalyst is. The ARI is measured by adding 6.0±0.1 g of catalyst having a particles size ranging from 53 to 125 microns to a hardened steel attrition cup. Approximately 24,000 scc/min of nitrogen gas is bubbled through a water-containing bubbler to humidify the nitrogen. The wet nitrogen passes through the attrition cup, and exits the attrition apparatus through a porous fiber thimble. The flowing nitrogen removes the finer particles, with the larger particles being retained in the cup. The porous fiber thimble separates the fine catalyst particles from the nitrogen that exits through the thimble. The fine particles remaining in the thimble represent catalyst that has broken apart through attrition.

The nitrogen flow passing through the attrition cup is maintained for 1 hour. The fines collected in the thimble are removed from the unit. A new thimble is then installed. The catalyst left in the attrition unit is attrited for an additional 3 hours, under the same gas flow and moisture levels. The fines collected in the thimble are recovered. The collection of fine catalyst particles separated by the thimble after the first hour are weighed. The amount in grams of fine particles divided by the original amount of catalyst charged to the attrition cup expressed on per hour basis is the ARI, in wt %/hr.

$$ARI=C/(B+C)/D\times 100\%$$

wherein

B=weight of catalyst left in the cup after the attrition test

C=weight of collected fine catalyst particles after the first hour of attrition treatment D=duration of treatment in hours after the first hour attrition treatment.

In one embodiment, the formulated catalyst composition has an attrition resistance index of not greater than 0.5 wt %/hr. Preferably, wherein the catalyst composition has an attrition resistance index (ARI) of not greater than 0.4 wt %/hr, and more preferably not greater than 0.3 wt %/hr.

The catalyst composition of the invention also has a relatively high density relative to conventional catalysts. In particular, the catalyst composition of the invention has a relatively high apparent bulk density (ABD) relative to conventional catalysts.

According to the invention, one way of measuring ABD was using the following procedure. A KIMAX graduated cylinder from KAMLE USA, accurate to 0.05 cc and having a 25 cc capacity, was used to weigh catalyst. The empty cylinder was weighed and the weight recorded as $W_a$. Approximately 25 cc of spray dried and calcined catalyst was poured into the cylinder, and the cylinder was tapped against a lab bench surface at a frequency of 160-170 times per minute for 30 seconds to pack the cylinder into the cylinder. The weight of the packed cylinder was weighed and recorded as $W_b$. The volume of the catalyst in the cylinder was determined by reading the level of the packed catalyst in the cylinder and recorded as $V_c$. ABD was then calculated as $ABD=(W_b-W_a)/V_c$.

In one embodiment, the catalyst composition has an apparent bulk density (ABD) of at least 0.83 g/cc. Preferably, the catalyst composition has an ABD at least 0.84 g/cc, more preferably at least 0.85 g/cc, and most preferably at least 0.86 g/cc. Generally, the catalyst density is not significantly greater than water. In one embodiment, the catalyst composition has an ABD not greater than 1 g/cc. Preferably, the catalyst composition has an ABD not greater than 0.99 g/cc, and more preferably not greater than 0.98 g/cc.

The catalyst composition of this invention is a dried catalyst composition. It can be dried so that it retains a template within the pore structure of the molecular sieve component, such as by spray drying, or it can be further dried, such as by calcining, which removes the template from the pore structure. Because the dried catalyst is attrition resistant, it is not necessary to calcine the formulated composition prior to use. For example, the dried composition can be loaded into a reaction system so that conditions within the system remove the template to activate the catalyst for use during operation of the reaction process.

III. Methods of Making Catalyst

A. Making Molecular Sieve Crystals

Generally, molecular sieves (i.e., molecular sieve crystals) are synthesized by the hydrothermal crystallization of one or more of a source of aluminum, a source of phosphorus, a source of silicon, water and a templating agent, such as a nitrogen containing organic compound. Typically, a combination of sources of silicon and aluminum, or silicon, aluminum and phosphorus, water and one or more templating agents, is placed in a sealed pressure vessel. The vessel is optionally lined with an inert plastic such as polytetrafluoroethylene, and heated under a crystallization pressure and temperature, until a crystalline material is formed, which can then recovered by filtration, centrifugation and/or decanting.

Non-limiting examples of silicon sources include silicates, fumed silica, for example, Aerosil-200 available from Degussa Inc., New York, N.Y., and CAB-O-SIL M-5, organosilicon compounds such as tetraalkylorthosilicates, for example, tetramethylorthosilicate (TMOS) and tetraethylorthosilicate (TEOS), colloidal silicas or aqueous suspensions thereof, for example Ludox-HS-40 sol available from E.I. du Pont de Nemours, Wilmington, Del., silicic acid or any combination thereof.

Non-limiting examples of aluminum sources include aluminum alkoxides, for example aluminum isopropoxide, aluminum phosphate, aluminum hydroxide, sodium aluminate, pseudo-boehmite, gibbsite and aluminum trichloride, or any combination thereof. A convenient source of aluminum is pseudo-boehmite, particularly when producing a silicoaluminophosphate molecular sieve.

Non-limiting examples of phosphorus sources, which may also include aluminum-containing phosphorus compositions, include phosphoric acid, organic phosphates such as triethyl phosphate, and crystalline or amorphous aluminophosphates such as $AlPO_4$, phosphorus salts, or combinations thereof. A convenient source of phosphorus is phosphoric acid, particularly when producing a silicoaluminophosphate.

In general, templating agents or templates include compounds that contain elements of Group 15 of the Periodic Table of Elements, particularly nitrogen, phosphorus, arsenic and antimony. Typical templates also contain at least one alkyl or aryl group, such as an alkyl or aryl group having from 1 to 10 carbon atoms, for example from 1 to 8 carbon atoms. Preferred templates are nitrogen-containing compounds, such as amines, quaternary ammonium compounds and combinations thereof. Suitable quaternary ammonium compounds are represented by the general formula $R_4N^+$, where each R is hydrogen or a hydrocarbyl or substituted hydrocarbyl group, preferably an alkyl group or an aryl group having from 1 to 10 carbon atoms.

Non-limiting examples of templates include tetraalkyl ammonium compounds including salts thereof, such as tetramethyl ammonium compounds, tetraethyl ammonium compounds, tetrapropyl ammonium compounds, and tetrabutylammonium compounds, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N',N',N,N-tetramethyl-(1,6)hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2)octane ion; di-n-butylamine, neopentylamine, di-n-pentylamine, isopropylamine, t-butyl-amine, ethylenediamine, pyrrolidine, and 2-imidazolidone. Preferred templates are selected from the group consisting of tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine, heated degraded forms thereof, and combinations thereof.

The pH of the synthesis mixture containing at a minimum a silicon, aluminum, optionally a phosphorus composition, and a templating agent, is generally in the range of from 2 to 10, such as from 4 to 9, for example from 5 to 8.

Generally, the synthesis mixture described above is sealed in a vessel and heated, preferably under autogenous pressure, to a temperature in the range of from about 80° C. to about 250° C., such as from about 100° C. to about 250° C., for example from about 125° C. to about 225° C., such as from about 150° C. to about 180° C.

In one embodiment, the synthesis of molecular sieve crystalline particles is aided by seeds from another or the same framework type molecular sieve.

The time required to form the crystalline particles is usually dependent on the temperature and can vary from immediately up to several weeks. Typically, the crystallization time is from about 30 minutes to around 2 weeks, such as from about 45 minutes to about 240 hours, for example from about 1 hour to about 120 hours. The hydrothermal crystallization may be carried out with or without agitation or stirring.

One method for crystallization involves subjecting an aqueous reaction mixture containing an excess amount of a templating agent to crystallization under hydrothermal conditions, establishing an equilibrium between molecular sieve formation and dissolution, and then, removing some of the excess templating agent and/or organic base to inhibit dissolution of the molecular sieve. See, for example, U.S. Pat. No. 5,296,208, which is herein fully incorporated by reference.

Other methods for synthesizing molecular sieves or modifying molecular sieves are described in U.S. Pat. No. 5,879,655 (controlling the ratio of the templating agent to phosphorus), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorus modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), PCT WO 01/36329 published May 25, 2001 (surfactant synthesis), PCT WO 01/25151 published Apr. 12, 2001 (staged acid addition), PCT WO 01/60746 published Aug. 23, 2001 (silicon oil), U.S. Patent Application Publication No. 20020055433 published May 9, 2002 (cooling molecular sieve), U.S. Pat. No. 6,448,197 (metal impregnation including copper), U.S. Pat. No. 6,521,562 (conductive microfilter), and U.S. Patent Application Publication No. 20020115897 published Aug. 22, 2002 (freeze drying the molecular sieve), which are all herein fully incorporated by reference.

Once the crystalline molecular sieve product is formed, usually in a slurry state, it may be recovered by any standard technique well known in the art, for example, by centrifugation or filtration. The recovered crystalline particle product, normally termed the "wet filter cake", may then be washed, such as with water, and then dried, such as in air, before being formulated into a catalyst composition. Alternatively, the wet filter cake may be formulated into a catalyst composition directly, that is without any drying, or after only partial drying.

B. Making Formulated Molecular Sieve Catalyst

1. Components of Formulated Molecular Sieve Catalyst

Molecular sieve catalyst, which contains molecular sieve crystal product, binder and matrix materials, is also referred to as a formulated catalyst. It is made by mixing together molecular sieve crystals (which preferably includes template) and a liquid, with matrix material and binder, to form a slurry. The slurry is then dried (i.e., liquid is removed), without completely removing the template from the molecular sieve. Since this dried molecular sieve catalyst includes template, it has not been activated, and is considered a preformed catalyst. The catalyst in this form is resistant to catalytic loss by contact with moisture or water. However, the preformed catalyst must be activated before use, and this invention provides appropriate methods of activating, preferably by further heat treatment, to maintain a low water content within the activated catalyst.

The liquid used to form the slurry can be any liquid conventionally used in formulating molecular sieve catalysts. Non-limiting examples of suitable liquids include water, alcohol, ketones, aldehydes, esters, or a combination thereof. Water is a preferred liquid.

Matrix materials are included in the slurry used to make the formulated molecular sieve catalyst of this invention. Such materials are typically effective as thermal sinks assisting in shielding heat from the catalyst composition, for example, during regeneration. They can further act to densify the catalyst composition, increase catalyst strength such as crush strength and attrition resistance, and to control the rate of conversion in a particular process. Non-limiting examples of matrix materials include one or more of: rare earth metals, metal oxides including titania, zirconia, magnesia, thoria, beryllia, quartz, silica or sols, and mixtures thereof, for example, silica-magnesia, silica-zirconia, silica-titania, silica-alumina and silica-alumina-thoria.

One preferred type of matrix material used to make the catalyst of this invention is clay. Particularly preferred clays include kaolins such as, for example, Dixie, McNamee, Georgia and Florida clays. Optionally, the matrix material, preferably any of the clays, are calcined, acid treated, and/or chemical treated before being used as a slurry component.

In a particular embodiment, the clay has a low iron or titania content, and is most preferably kaolin clay. Kaolin has been found to form a pumpable, high solid content slurry; it has a low fresh surface area, and it packs together easily due to its platelet structure.

Preferably, the clay has an average particle size of from about 0.05 μm to about 0.75 μm; more preferably from about 0.1 μm to about 0.6 μm. It is also desirable that the clay material have a $d_{90}$ particle size distribution of less than about 1.5 μm, preferably less than about 1 μm.

Binders are also included in the slurry used to make the formulated molecular sieve catalyst of this invention. In one embodiment of the invention, the binder is an alumina-containing sol, preferably aluminium chlorohydrate. Upon calcining, the inorganic oxide sol, is converted into an inorganic oxide matrix component, which is particularly effective in forming an attrition resistant molecular sieve catalyst composition. For example, an alumina sol will convert to an aluminium oxide matrix following heat treatment.

Aluminium chlorohydrate, a hydroxylated aluminium based sol containing a chloride counter ion, also known as aluminium chlorohydrol, has the general formula $$Al_mO_n(OH)_oCl_p \cdot x(H_2O)$$

wherein m is 1 to 20, n is 1 to 8, o is 5 to 40, p is 2 to 15, and x is 0 to 30. In one embodiment, the binder is $Al_{13}O_4$ $(OH)_{24}Cl_7 \cdot 12(H_2O)$ as is described in G. M. Wolterman, et al., *Stud. Surf. Sci. and Catal.*, 76, pages 105-144, Elsevier, Amsterdam, 1993, which is herein incorporated by reference. In another embodiment, one or more binders are present in combination with one or more other non-limiting examples of alumina materials such as aluminium oxyhydroxide, γ-alumina, boehmite and transitional aluminas such as α-alumina, β-alumina, γ-alumina, δ-alumina, ε-alumina, κ-alumina, and ρ-alumina, aluminium trihydroxide, such as gibbsite, bayerite, nordstrandite, doyelite, and mixtures thereof.

Aluminum chlorohydrate can prepared by dissolving either metallic aluminum or hydrated alumina in hydrochloric acid under controlled conditions, and is available commercially in different forms, such as solid products; for example, the solid of chemical formula $Al_2(OH)_5Cl.n(H_2O)$ or as pre-prepared, commercially available, aqueous solutions. Other non-limiting examples of useful aluminum oxide precursors that may be used according to this invention include aluminum hexahydrate, aluminum pentachlorohydrate ($Al_2(OH)Cl_5$), aluminum tetrachlorohydrate ($Al_2(OH)_2Cl_4$), aluminum trichlorohydrate ($Al_2(OH)_3Cl_3$), aluminum dichlorohydrate ($Al_2(OH)_4Cl_2$), aluminum sesquichlorohydrate ($Al_2(OH)_{4.5}Cl_{1.5}$).

Other non-limiting examples of binders useful according to this invention include precursors of aluminum-zirconium oxides. Such precursors include, but are not limited to, aluminum zirconium chlorohydrates; for example, aluminum zirconium trichlorohydrate, aluminum zirconium tetrachlorohydrate, aluminum zirconium pentachlorohydrate, aluminum zirconium octachlorohydrate, aluminum zirconium chlorhydrex, aluminum zirconium chlorhydrex glycine complexes (e.g., aluminum zirconium trichlorohydrex glycine complex, aluminum zirconium tetrachlorohydrex glycine complex, aluminum zirconium pentachlorohydrex glycine complex, and aluminum zirconium octachlorohydrex glycine complex). In the absence of glycine, these materials form gels in aqueous solutions. Reheis Chemicals Inc., Berkeley Heights, N.J. produces a variety of aluminum zirconium chlorohydrates. These materials can be prepared from a variety of zirconium starting materials such as zirconyl chloride ($ZrOCl_2$), zirconyl hydroxychloride ($ZrO(OH)Cl$), zirconium hydroxy carbonate paste ($ZrO(OH)(CO_3)_{0.5}$), and combinations of these zirconium starting materials, with a hydrated aluminum solution, such as a solution of aluminum chlorohydrate, aluminum hexahydrate, aluminum sesquichlorohydrate or aluminum dichlorohydrate solution, or a solution obtained by combining one or several of these aluminum species solutions.

In another embodiment, the binders are alumina sols, predominantly comprising aluminium oxide, optionally including silicon. In yet another embodiment, the binders are peptised alumina made by treating alumina hydrates such as pseudobohemite, with an acid, preferably a non-halogen acid, to prepare sols or aluminium ion solutions. Non-limiting examples of commercially available colloidal alumina sols include Nalco 8676 available from Nalco Chemical Co., Naperville, Ill., and Nyacol available from the Nyacol Nano Technology Inc., Boston, Mass.

In a preferred embodiment, the amount of binder used to prepare the molecular sieve catalyst composition is at least 5 wt %, based on total weight of the material used to make the composition, excluding liquid (i.e., after drying), particularly excluding water. Preferably the amount of binder used to prepare the molecular sieve catalyst is at least 8 wt %, and more preferably at least 10 wt %, based on total weight of the material used in making the catalyst, excluding liquid (i.e., after drying). It is also preferred that the amount of binder used to prepare the molecular sieve catalyst is not greater than about 50 wt %, preferably not greater than 40 wt %, and more preferably not greater than 30 wt %, based on total weight of the material used in making the catalyst, excluding liquid (i.e., after drying).

2. Making a Slurry with Molecular Sieve Crystals

The molecular sieve crystals are mixed with clay and binder, as well as liquid solvent component, to form a slurry. The components can be mixed in any order, and the mixture is thoroughly stirred to form the slurry. The more thorough the stirring, the better the consistency of the slurry, and the more uniform will be the dried catalyst composition.

The molecular sieve crystals, clay and binder are mixed together at a breakage energy effective to break apart agglomerates and aggregates, as defined in *Practical Dispersion*, R. F. Conley, VCH, New York, p. 213, 1996, which is incorporated herein by reference. Mixers capable of mixing together components at the appropriate breakage energy include impeller mills, ball mills, stirred media mills, vibratory mills, multiple roll mills and ultrasonic dispersion devices. Further description of appropriate mixing equipment is described in *Solid-Liquid Dispersions*, B. Dobias et al., pp. 22-27, Marcel Dekker, New York, 1999, which is incorporated herein by reference.

In one embodiment, the molecular sieve crystals, clay and binder are mixed together at the appropriate breakage energy using a bead mill mixer. Preferably, the bead mill mixer incorporates beads in the mixing portion of the mixer having a relative span factor (RSF) that is relatively low, meaning that there is small variation in bead diameter. The RSF is calculated as $RSF=(d_{90}-d_{10})/d_{50}$, wherein $d_{90}$ refers to particle diameter at 90% particle distribution, $d_{10}$ refers to particle diameter at 10% particle distribution, and $d_{50}$ refers to particle diameter at 50% particle distribution. Preferably, the beads have a RSF of not greater than 0.2, more preferably not greater than 0.15, and most preferably not greater than 0.1.

In one embodiment, the components used to make the molecular sieve catalyst composition are mixed at breakage energy of at least $10^{-5}$ cal cm$^{-2}$. Preferably, the components used to make the molecular sieve catalyst composition are mixed at breakage energy of at least $5\times10^{-4}$ cal cm$^{-2}$, and more preferably at least $10^{-4}$ cal cm$^{-2}$.

The breakage energy should high enough to obtain the desired characteristics of the invention. However, the breakage energy should not be so high as to break apart chemical bonds. In another embodiment, the components used to make the molecular sieve catalyst composition are mixed at breakage energy of not greater than $10^{-1}$ cal cm$^{-2}$. Preferably, the components used to make the molecular sieve catalyst composition are mixed at breakage energy of not greater than $6\times10^{-2}$ cal cm$^{-2}$, and more preferably not greater than $5\times10^{-2}$ cal cm$^{-2}$. Bead mills typically generate a breakage energy of $6\times10^{-5}$ to $6\times10^{-2}$ cal cm$^{-2}$, whereas impeller mills typically generate a breakage energy of $10^{-5}$ to $2\times10^{-4}$ cal cm$^{-2}$, and ball mills generate a breakage energy of $10^{-5}$ to $6\times10^{-3}$ cal cm$^{-2}$.

In one embodiment, the slurry has a viscosity of at least 400 cP (0.4 Pa/sec), as measured using a Brookfield LV-DVE viscometer with a No. 3 spindle at 10 rpm. Preferably, the slurry has a viscosity of at least 500 cP (0.5 Pa/sec), more preferably at least 600 cP (0.6 Pa/sec), and most preferably at least 700 cP (0.7 Pa/sec), as measured using a Brookfield LV-DVE viscometer with a No. 3 spindle at 10 rpm. It is also preferred that the slurry have a viscosity that is not greater than 12,500 cP (12.5 Pa/sec), as measured using a Brookfield LV-DVE viscometer with a No. 3 spindle at 10 rpm. Preferably, the slurry has a viscosity not greater than 11,000 cP (11 Pa/sec), and more preferably not greater than 10,500 cP (10.5 Pa/sec), as measured using a Brookfield LV-DVE viscometer with a No. 3 spindle at 10 rpm.

In another embodiment, the slurry has a solids content of at least 40 wt %, based on total weight of the slurry mixture. Preferably, the slurry has a solids content of at least 41 wt %, more preferably at least 42 wt %, and most preferably at least 42.5 wt %, based on the total weight of the slurry. The solids content can be measured using any conventional means. However, a CEM MAS 700 microwave muffle furnace is particularly preferred to give results consistent with the values recited herein. It is also preferred that the slurry have a solids content of not greater than 60 wt %, based on total weight of the slurry. Preferably, the slurry has a solids content of not greater than 58 wt %, more preferably not greater than 56 wt %, and most preferably not greater than 54 wt % based on total weight of the slurry.

In another embodiment of the invention, the molecular sieve crystals, clay and binder are mixed together to form a slurry mixture at a binder to molecular sieve weight ratio of at least 0.20:1. Preferably, the molecular sieve crystals, clay and binder are mixed together at a binder to molecular sieve weight ratio of at least 0.22:1, more preferably at least 0.24:1, and most preferably at least 0.25:1. It is also preferred that the crystals, clay and binder be mixed together at a binder to molecular sieve weight ratio of not greater than 0.8:1, preferably not greater than 0.6:1.

In another embodiment, the molecular sieve crystals, clay and binder are mixed together to form a slurry mixture at a binder content of at least 5 wt %, preferably at least 8 wt %, and more preferably at least 10 wt %, based on total weight of the mixture, excluding liquid (e.g., water). It is also preferred in an embodiment that the molecular sieve crystals, clay and binder are mixed together to form a slurry mixture at a binder content of not greater than 30 wt %, preferably not greater than 25 wt %, based on total weight of the mixture, excluding liquid (e.g., water).

In one embodiment of the invention, the slurry is aged prior to drying. In this embodiment, aging means submitting the catalyst formulation slurry to a mild thermal treatment, with or without agitation and/or stirring and/or mixing. The duration of the thermal treatment should be sufficient to allow the generation of the reactive ionic species at a sufficient rate and in an amount sufficient to allow the best attrition resistance properties in the catalyst particles.

Conditions of duration and temperature that achieve this result include: maintaining the catalyst formulation slurry at a temperature of from 0° C. to 100° C., preferably of from 10° C. to 90° C., more preferably of from 15° C. to 80° C., most preferably of from 20° C. to 70° C. The duration of this mild thermal treatment can vary, depending on various factors such as the type of inorganic oxide precursor, the concentration of the inorganic precursor and the temperature. The higher the temperature and the lower the concentration in inorganic oxide precursor, the less time will be required to achieve the proper level of aging of the catalyst formulation slurry according to the invention. Periods of aging will typically be at least 2 hours, preferably at least 4 hours, more preferably at least 5 hours, and most preferably at least 6 hours. In a preferred embodiment, aging of the catalyst formulation slurry is performed for not more than 150 hours, preferably not more than 120 hours, most preferably not more than 100 hours. If aging takes place at a temperature of from 30° C. to 50° C., aging of the catalyst formulation preferably takes place for a period of from 4 hours to 80 hours, preferably of from 5 hours to 75 hours, more preferably of from 5.5 hours to 50 hours, most preferably of from 6 hours to 36 hours.

3. Drying the Slurry

In one embodiment, the slurry of the molecular sieve, binder and matrix materials is fed to a forming unit that produces a dried molecular sieve catalyst composition. Non-limiting examples of forming units include spray dryers, pelletizers, extruders, etc. In a preferred embodiment, the forming unit is spray dryer. Typically, the forming unit is maintained at a temperature sufficient to remove most of the liquid (e.g., water) from the slurry.

When a spray dryer is used as the forming (or drying) unit, typically, the slurry of the molecular sieve, matrix material and binder, is co-fed to the drying unit with a drying gas. In one embodiment the drying unit has an average inlet temperature ranging from 150° C. to 550° C., and an average outlet temperature ranging from 100° C. to about 250° C.

In one embodiment, the slurry is passed through a nozzle distributing the slurry into small droplets, resembling an aerosol spray, into a drying chamber. Atomization is achieved by forcing the slurry through a single nozzle or multiple nozzles with a pressure drop in the range of from 100 psia to 1000 psia (690 kPaa to 6895 kpaa). In another embodiment, the slurry is co-fed through a single nozzle or multiple nozzles along with an atomization fluid such as air, steam, flue gas, or any other suitable gas.

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a partially, substantially or totally dried molecular sieve catalyst composition.

An example of a spray drying process that may be used to dry the slurry is disclosed in U.S. Pat. No. 4,946,814, the description of which is incorporated herein by reference.

In another embodiment of the invention, the slurry is dried in a drying unit and then calcined. In one embodiment, the slurry is dried to form a dried molecular sieve catalyst composition, and the dried catalyst composition is calcined. In general, calcination further hardens and/or activates the dried molecular sieve catalyst composition. An acceptable calcination environment is air that typically includes a small amount of water vapour. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

The dried or formulated molecular sieve catalyst composition can be calcined in many types of devices, including but not limited to, rotary calciners, fluid bed calciners, batch ovens, and the like. Calcination time is typically dependent on the degree of hardening of the molecular sieve catalyst composition and the temperature.

In a preferred embodiment, the molecular sieve catalyst composition is heated in nitrogen at a temperature of from about 600° C. to about 700° C. Heating is carried out for a period of time typically from 30 minutes to 15 hours, preferably from 1 hour to about 10 hours, more preferably from about 1 hour to about 5 hours, and most preferably from about 2 hours to about 4 hours.

Other methods for calcining or activating a molecular sieve catalyst composition are described in, for example, U.S. Pat. No. 5,185,310 (heating molecular sieve of gel alumina and water to 450° C.), and PCT WO 00/75072 published Dec. 14, 2000 (heating to leave an amount of template), which are all herein fully incorporated by reference IV. Methods of Using Catalyst The molecular sieve catalyst product made according to this invention is useful in a variety of processes including cracking of, for example, a naphtha feed to light olefin(s)

(U.S. Pat. No. 6,300,537) or higher molecular weight (MW) hydrocarbons to lower MW hydrocarbons; hydrocracking of, for example, heavy petroleum and/or cyclic feedstock; isomerization of, for example, aromatics such as xylene; polymerization of, for example, one or more olefin(s) to produce a polymer product; reforming; hydrogenation; dehydrogenation; dewaxing of, for example, hydrocarbons to remove straight chain paraffins; absorption of, for example, alkyl aromatic compounds for separating out isomers thereof; alkylation of, for example, aromatic hydrocarbons such as benzene and alkyl benzene, optionally with propylene to produce cumene or with long chain olefins; transalkylation of, for example, a combination of aromatic and polyalkylaromatic hydrocarbons; dealkylation; hydrodecyclization; disproportionation of, for example, toluene to make benzene and paraxylene; oligomerization of, for example, straight and branched chain olefin(s); and dehydrocyclization.

Preferred processes include processes for converting naphtha to highly aromatic mixtures; converting light olefin(s) to gasoline, distillates and lubricants; converting oxygenates to olefin(s); converting light paraffins to olefins and/or aromatics; and converting unsaturated hydrocarbons (ethylene and/or acetylene) to aldehydes for conversion into alcohols, acids and esters.

The most preferred process of the invention is a process directed to the conversion of a feedstock to one or more olefin(s). Typically, the feedstock contains one or more aliphatic-containing compounds such that the aliphatic moiety contains from 1 to about 50 carbon atoms, such as from 1 to 20 carbon atoms, for example from 1 to 10 carbon atoms, and particularly from 1 to 4 carbon atoms.

Non-limiting examples of aliphatic-containing compounds include alcohols such as methanol and ethanol, alkyl mercaptans such as methyl mercaptan and ethyl mercaptan, alkyl sulfides such as methyl sulfide, alkylamines such as methylamine, alkyl ethers such as dimethyl ether, diethyl ether and methylethyl ether, alkyl halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) produced from the feedstock typically have from 2 to 30 carbon atoms, preferably 2 to 8 carbon atoms, more preferably 2 to 6 carbon atoms, still more preferably 2 to 4 carbons atoms, and most preferably are ethylene and/or propylene.

The catalyst composition of the invention is particularly useful in the process that is generally referred to as the gas-to-olefins (GTO) process or, alternatively, the methanol-to-olefins (MTO) process. In this process, an oxygenated feedstock, most preferably a methanol-containing feedstock, is converted in the presence of a molecular sieve catalyst composition into one or more olefin(s), preferably and predominantly, ethylene and/or propylene.

Using the catalyst composition of the invention for the conversion of a feedstock, preferably a feedstock containing one or more oxygenates, the amount of olefin(s) produced based on the total weight of hydrocarbon produced is greater than 50 weight percent, typically greater than 60 weight percent, such as greater than 70 weight percent, and preferably greater than 75 weight percent. In one embodiment, the amount of ethylene and/or propylene produced based on the total weight of hydrocarbon product produced is greater than 65 weight percent, such as greater than 70 weight percent, for example greater than 75 weight percent, and preferably greater than 78 weight percent. Typically, the amount ethylene produced in weight percent based on the total weight of hydrocarbon product produced, is greater than 30 weight percent, such as greater than 35 weight percent, for example greater than 40 weight percent. In addition, the amount of propylene produced in weight percent based on the total weight of hydrocarbon product produced is greater than 20 weight percent, such as greater than 25 weight percent, for example greater than 30 weight percent, and preferably greater than 35 weight percent.

In addition to the oxygenate component, such as methanol, the feedstock may contains one or more diluent(s), which are generally non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example water, may be used either in a liquid or a vapor form, or a combination thereof. The diluent may be either added directly to the feedstock entering a reactor or added directly to the reactor, or added with the molecular sieve catalyst composition.

The present process can be conducted over a wide range of temperatures, such as in the range of from about 200° C. to about 1000° C., for example from about 250° C. to about 800° C., including from about 250° C. to about 750° C., conveniently from about 300° C. to about 650° C., typically from about 350° C. to about 600° C. and particularly from about 350° C. to about 550° C.

Similarly, the present process can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kPaa.

The weight hourly space velocity (WHSV), defined as the total weight of feedstock excluding any diluents per hour per weight of molecular sieve in the catalyst composition, typically ranges from about 1 $hr^{-1}$ to about 5000 $hr^{-1}$, such as from about 2 hr$^{-1}$ to about 3000 hr$^{-1}$, for example from about 5 hr$^{-1}$ to about 1500 hr$^{-1}$, and conveniently from about 10 hr$^{-1}$ to about 1000 hr$^{-1}$. In one embodiment, the WHSV is greater than 20 hr$^{-1}$ and, where feedstock contains methanol and/or dimethyl ether, is in the range of from about 20 hr$^{-1}$ to about 300 hr$^{-1}$.

Where the process is conducted in a fluidized bed, the superficial gas velocity (SGV) of the feedstock including diluent and reaction products within the reactor system, and particularly within a riser reactor(s), is at least 0.1 meter per second (m/sec), such as greater than 0.5 m/sec, such as greater than 1 m/sec, for example greater than 2 m/sec, conveniently greater than 3 m/sec, and typically greater than 4 m/sec. See for example U.S. patent application Ser. No. 09/708,753 filed Nov. 8, 2000, which is herein incorporated by reference.

The process of the invention is conveniently conducted as a fixed bed process, or more typically as a fluidized bed process (including a turbulent bed process), such as a continuous fluidized bed process, and particularly a continuous high velocity fluidized bed process.

The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor types are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one practical embodiment, the process is conducted as a fluidized bed process or high velocity fluidized bed process utilizing a reactor system, a regeneration system and a recovery system.

In such a process the reactor system conveniently includes a fluid bed reactor system having a first reaction zone within one or more riser reactor(s) and a second reaction zone within at least one disengaging vessel, typically comprising one or more cyclones. In one embodiment, the one or more riser reactor(s) and disengaging vessel are contained within a single reactor vessel. Fresh feedstock, preferably containing one or more oxygenates, optionally with one or more diluent(s), is fed to the one or more riser reactor(s) into which a molecular sieve catalyst composition or coked version thereof is introduced. In one embodiment, prior to being introduced to the riser reactor(s), the molecular sieve catalyst composition or coked version thereof is contacted with a liquid, preferably water or methanol, and/or a gas, for example, an inert gas such as nitrogen.

In an embodiment, the amount of fresh feedstock fed as a liquid and/or a vapor to the reactor system is in the range of from 0.1 weight percent to about 85 weight percent, such as from about 1 weight percent to about 75 weight percent, more typically from about 5 weight percent to about 65 weight percent based on the total weight of the feedstock including any diluent contained therein. The liquid and vapor feedstocks may be the same composition, or may contain varying proportions of the same or different feedstocks with the same or different diluents.

The feedstock entering the reactor system is preferably converted, partially or fully, in the first reactor zone into a gaseous effluent that enters the disengaging vessel along with the coked catalyst composition. In the preferred embodiment, cyclone(s) are provided within the disengaging vessel to separate the coked catalyst composition from the gaseous effluent containing one or more olefin(s) within the disengaging vessel. Although cyclones are preferred, gravity effects within the disengaging vessel can also be used to separate the catalyst composition from the gaseous effluent. Other methods for separating the catalyst composition from the gaseous effluent include the use of plates, caps, elbows, and the like.

In one embodiment, the disengaging vessel includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to the regeneration system.

The coked catalyst composition is withdrawn from the disengaging vessel and introduced to the regeneration system. The regeneration system comprises a regenerator where the coked catalyst composition is contacted with a regeneration medium, preferably a gas containing oxygen, under conventional regeneration conditions of temperature, pressure and residence time.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example from about 450° C. to about 750° C., and conveniently from about 550° C. to 700° C. The regeneration pressure may be in the range of from about 15 psia (103 kPaa) to about 500 psia (3448 kPaa), such as from about 20 psia (138 kPaa) to about 250 psia (1724 kPaa), including from about 25 psia (172 kPaa) to about 150 psia (1034 kPaa), and conveniently from about 30 psia (207 kPaa) to about 60 psia (414 kPaa).

The residence time of the catalyst composition in the regenerator may be in the range of from about one minute to several hours, such as from about one minute to 100 minutes, and the volume of oxygen in the regeneration gas may be in the range of from about 0.01 mole percent to about 5 mole percent based on the total volume of the gas.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system. Other methods for operating a regeneration system are in disclosed U.S. Pat. No. 6,290,916 (controlling moisture), which is herein fully incorporated by reference.

The regenerated catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In one embodiment, the regenerated catalyst composition withdrawn from the regeneration system is returned to the riser reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more riser reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, *Experimental Techniques, Circulating Fluidized Beds,* Grace, Avidan and Knowlton, eds., Blackie, 1997 (336-337), which is herein incorporated by reference.

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example from about 0.2 weight percent to about 5 weight percent, and conveniently from about 0.3 weight percent to about 2 weight percent based on the weight of the molecular sieve.

The gaseous effluent is withdrawn from the disengaging system and is passed through a recovery system. There are many well-known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment, for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a dethanizer, a depropanizer, a wash tower often referred to as a caustic wash tower and/or quench tower, absorbers, adsorbers, membranes, ethylene splitter, propylene splitter and butene splitter.

Various recovery systems useful for recovering olefin(s), such as ethylene, propylene and/or butene, are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Other recovery systems that include purification systems, for example for the purification of olefin(s), are described in *Kirk-Othmer Encyclopedia of Chemical Technology,* 4th Edition, Volume 9, John Wiley & Sons, 1996, pages 249-271 and 894-899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which are herein incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Typically, in converting one or more oxygenates to olefin(s) having 2 or 3 carbon atoms, a minor amount hydrocarbons, particularly olefin(s), having 4 or more carbon atoms is also produced. The amount of $C_4$+ hydrocarbons is normally less than 20 weight percent, such as less than 10 weight percent, for example less than 5 weight percent, and particularly less than 2 weight percent, based on the total weight of the effluent gas withdrawn from the process, excluding water. Typically, therefore the recovery system may include one or more reaction systems for converting the $C_4$+ impurities to useful products.

Non-limiting examples of such reaction systems are described in U.S. Pat. No. 5,955,640 (converting a four carbon product into butene-1), U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading C3, C4 and C5 Olefinic Streams,* Pet. & Coal, Vol. 37, No. 4 (1995) (dimerizing or oligomerizing propylene, butylene and pentylene), which are all fully herein incorporated by reference.

The preferred light olefin(s) produced by any one of the processes described above are high purity prime olefin(s) products that contain a single carbon number olefin in an amount greater than 80 percent, such as greater than 90 weight percent, such as greater than 95 weight percent, for example at least about 99 weight percent, based on the total weight of the olefin.

In one practical embodiment, the process of the invention forms part of an integrated process for producing light olefin(s) from a hydrocarbon feedstock, preferably a gaseous hydrocarbon feedstock, particularly methane and/or ethane. The first step in the process is passing the gaseous feedstock, preferably in combination with a water stream, to a syngas production zone to produce a synthesis gas (syngas) stream, typically comprising carbon dioxide, carbon monoxide and hydrogen. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material. Preferably synthesis gas stream is produced via steam reforming of natural gas.

The next step in the process involves contacting the synthesis gas stream generally with a heterogeneous catalyst, typically a copper based catalyst, to produce an oxygenate containing stream, often in combination with water. In one embodiment, the contacting step is conducted at temperature in the range of from about 150° C. to about 450° C. and a pressure in the range of from about 5 MPa to about 10 MPa.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fuel oil. The oxygenate containing stream, crude methanol, in the preferred embodiment is passed through a well known purification processes, distillation, separation and fractionation, resulting in a purified oxygenate containing stream, for example, commercial Grade A and AA methanol.

The oxygenate containing stream or purified oxygenate containing stream, optionally with one or more diluents, can then be used as a feedstock in a process to produce light olefin(s), such as ethylene and/or propylene. Non-limiting examples of this integrated process are described in EP-B-0 933 345, which is herein fully incorporated by reference.

In another more fully integrated process, that optionally is combined with the integrated processes described above, the olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Polymerization processes include solution, gas phase, slurry phase and a high pressure processes, or a combination thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above. However, the preferred polymerization catalysts are the Ziegler-Natta, Phillips-type, metallocene, metallocene-type and advanced polymerization catalysts, and mixtures thereof.

In a preferred embodiment, the integrated process comprises a process for polymerizing one or more olefin(s) in the presence of a polymerization catalyst system in a polymerization reactor to produce one or more polymer products, wherein the one or more olefin(s) have been made by converting an alcohol, particularly methanol, using a molecular sieve catalyst composition as described above. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

V. EXAMPLES OF METHODS OF MAKING CATALYST

Example 1

A slurry containing 45 wt % solid was prepared as follows: (a) adding 154.5 g of aluminum chlorohydrate (ACH) MicroDry (loss on ignition (LOI): 50.6%; from Reheis Inc., Berkeley Heights, N.J.) to 675.6 g of deionized water and mixing at 700 rpm for 10 minutes using a Yamato Model 2100 homogenizer (Yamato Scientific America Inc., Orangeburg, N.Y.) to give a solution having pH of 4.02 at 23.7° C.; (b) adding 349.9 g of molecular sieve 70V that was dried at 120° C. for 19 hrs (LOI of 17.69%) to the solution from step (a) and mixing at 700 rpm for 15 minutes using the Yamato homogenizer Model 2100 used in step (a), the slurry thus obtained having a pH of 3.72 measured at 28.6° C.; (c) adding 420 g of ASP Ultrafine kaolin clay (LOI: 15.31%, Engelhard Corporation, Iselin, N.J.), while mixing at 700 rpm using the Yamato Model 2100 homogenizer for 15 minutes, the resulting slurry having a pH of 3.63 at 30.8° C.; (d) passing the slurry from step (c) through a bead mill, Eiger mini bead mill model M250 (Eiger Machinery, Inc., Grayslake, Ill.) having a ceramic chamber and using a high density and high purity yttria-stabilized zirconia microbeads of 0.65 mm at 3000 rpm for a single pass, the slurry produced having a pH of 3.48 measured at 23° C. This slurry contained 45.35 wt % solids, the solids being comprised of 40% SAPO-34 sieve, 10.6% $Al_2O_3$, and 49.4% clay.

750 g of the slurry were then spray dried to produce a spray dried catalyst using a Yamato DL-41 spray dryer (Yamato Scientific America, Orangeburg, N.Y.). The spray dryer operated in a down spray mode using a 1 mm atomization nozzle. The spray drying conditions were: feed rate: 23-25 g/min; inlet temperature: 350° C.; atomization pressure: 1 bar; carrier gas (nitrogen) flow at 60% of full setting. Spray dried products were collected in a cyclone, and calcined in a muffle furnace at 650° C. in air for 2 hours. The calcined samples were used for attrition and particle size analysis. Attrition resistance of the calcined spray dry product was determined using the ARI method. Surface and core clay to alumina ratios were calculated using the EDS method described herein, with the average core clay to alumina ratio being 2.4. Various results are shown in Table 1.

Example 2

A slurry containing 45 wt % solid was prepared according to the following procedure: (a) adding 231.7 g of aluminum chlorohydrate (ACH) MicroDry (LOI: 50.6%; from Reheis Inc., Berkeley Heights, N.J.) to 643.4 g of deionized water and mixing at 700 rpm for 10 minutes using a Yamato Model 2100 homogenizer (Yamato Scientific America Inc., Orangeburg, N.Y.) to give a solution having pH of 3.79 at 24.6° C.; (b) adding 350.0 g of molecular sieve 70V dried at 180° C. for 96 hrs (LOI: 17.71%) to the solution from step (a) and mixing at 700 rpm for 15 minutes using the Yamato homogenizer Model 2100 used in step (a), the slurry thus obtained having a pH of 3.56 measured at 27.8° C.; (c) adding 374.9 g of ASP Ultrafine kaolin clay (LOI: 15.31%, Engelhard Corporation, Iselin, N.J.), while mixing at 700 rpm using the Yamato Model 2100 homogenizer for 15 minutes, the resulting slurry having a pH of 3.58 at 26.6° C.; (d) passing the slurry from step (c) through a bead mill, Eiger mini bead mill model M250 (Eiger Machinery, Inc., Grayslake, Ill.) having a ceramic chamber and using a high density and high purity yttria-stabilized zirconia microbeads of 0.65 mm at 3000 rpm for a single pass, the slurry produced having a pH of 3.16 measured at 23° C. This slurry was then aged in a water bath at 40° C. for 16 hrs. The aged slurry contained 45.03 wt % solids, the solids being comprised of 40% SAPO-34 sieve, 15.9% $Al_2O_3$, and 44.1% clay, and having a pH of 3.06 at 23° C. It was used for spray dry to produce a spray dried catalyst.

750 g of the slurry were then spray dried using a Yamato DL-41 spray dryer (Yamato Scientific America, Orangeburg, N.Y.). The spray dryer operated in a down spray mode using a 1 mm atomization nozzle. The spray drying conditions were: feed rate: 38-40 g/min; inlet temperature: 350° C.; atomization pressure: 1 bar; carrier gas (nitrogen) flow at 60% of full setting. Spray drie products were collected in a cyclone, and calcined in a muffle furnace at 650° C. in air for 2 hours. The calcined samples were used for attrition and particle size analysis. Attrition resistance of the calcined spray dry product was determined using the ARI method. Surface and core clay to alumina ratios were calculated using the EDS method described herein, with the average core clay to alumina ratio being 2.4. Various results are shown in Table 1.

Example 3

A slurry containing 40 wt % solid was prepared according to the following procedure: (a) adding 113.7 g of aluminum chlorohydrate (ACH) MicroDry (LOI: 50.6%; from Reheis Inc., Berkeley Heights, N.J.) to 162.4 g of deionized water and mixing at 700 rpm for 10 minutes using a Yamato Model 2100 homogenizer (Yamato Scientific America Inc., Orangeburg, New York) to give a solution having pH of 3.77 at 30.3° C.; (b) adding 335.2 g of molecular sieve 70V filtercake (LOI: 57.04%) to the solution from step (a) and mixing at 700 rpm for 30 minutes using the Yamato homogenizer Model 2100 used in step (a), the slurry thus obtained having a pH of 3.75 measured at 30.3° C.; (c) adding 80.0 g of ASP Ultrafine kaolin clay (LOI: 15.31%, Engelhard Corporation, Iselin, N.J.), while mixing at 700 rpm using the Yamato Model 2100 homogenizer; the resulting slurry became too thick to continue. 8.0 g of Calloway 3330 (Vulcan Chemical Inc., Montgomery, Ala.) was then added along with 32 g of water. Another 108.7 g of the ASP Ultrafine kaolin clay was then added; (d) passing the slurry from step (c) through a bead mill, Eiger mini bead mill model M250 (Eiger Machinery, Inc., Grayslake, Ill.) having a ceramic chamber and using a high density and high purity yttria-stabilized zirconia microbeads of 0.65 mm at 3000 rpm for a single pass. The slurry produced had a pH of 3.35 measured at 23° C., and contained 40.55 wt % solids, with 40% of the total solids being SAPO-34 sieve, 15.6% $Al_2O_3$, and 44.4% clay.

750 g of the slurry were then spray dried using a Yamato DL-41 spray dryer (Yamato Scientific America, Orangeburg, N.Y.). The spray dryer operated in a down spray mode using a 1 mm atomization nozzle. The spray drying conditions were: feed rate: 17-19 g/min; inlet temperature: 350° C.; atomization pressure: 1 bar; carrier gas (nitrogen) flow at 60% of full setting. Spray dried products were collected in a cyclone, and calcined in a muffle furnace at 650° C. in air for 2 hours. The calcined samples were used for attrition and particle size analysis. The spray dried product derived from Example 1 is labeled as SD-300-C1. The calcined samples were used for attrition and particle size analysis. Attrition resistance of the calcined spray dry product was determined using the AR1 method. Surface and core clay to alumina ratios were calculated using the EDS method described herein, with the average core clay to alumina ratio being 2.4. Various results are shown in Table 1.

Example 4

A slurry containing 45 wt % solid was prepared according to the following procedure: (a) adding 255.8 g of aluminum chlorohydrate (ACH) MicroDry (LOI: 50.6%; from Reheis Inc., Berkeley Heights, N.J.) to 329.4 of deionized water and 36 g of Calloway 3330 (Vulcan Chemical Inc., Montgomery, Ala.), and mixing at 700 rpm for 10 minutes using a Yamato Model 2100 homogenizer (Yamato Scientific America Inc., Orangeburg, N.Y.) to give a solution having pH of 3.80 at 25.9° C.; (b) adding 754.2 g of molecular sieve 70V filtercake (LOI: 57.04%) to the solution from step (a) and mixing at 700 rpm for 10 minutes using the Yamato homogenizer Model 2100 used in step (a), the slurry thus obtained having a pH of 4.02 measured at 25.0° C.; (c) adding 424.7 g of ASP Ultrafine kaolin clay (LOI: 15.31%, Engelhard Corporation, Iselin, N.J.), while mixing at 700 rpm using the Yamato Model 2100 homogenizer for 15 minutes, the resulting slurry having a pH of 3.10 at 34° C.; (d) passing the slurry from step (c) through a bead mill, Eiger mini bead mill model M250 (Eiger Machinery, Inc., Grayslake, Ill.) having a ceramic chamber and using a high density and high purity yttria-stabilized zirconia microbeads of 0.65 mm at 5000 rpm for a single pass (lower milling rates were not successful). This slurry was aged at 40° C. in a water bath for 16 hrs. The slurry was comprised of 41.28 wt % solids, of which 40% of the total weight of the solids was SAPO-34 sieve, 15.6% $Al_2O_3$, and 44.4% clay, having a pH of 3.49 measured at 23° C.

750 g of the slurry were then spray dried using a Yamato DL-41 spray dryer (Yamato Scientific America, Orangeburg, N.Y.). The spray dryer operated in a down spray mode using a 1 mm atomization nozzle. The spray drying conditions were: feed rate: 22-24 g/min; inlet temperature: 350° C.; atomization pressure: 1 bar; carrier gas (nitrogen) flow at 60% of full setting. Spray dried products were collected in a cyclone, and calcined in a muffle furnace at 650° C. in air for 2 hours. The calcined samples were used for attrition and particle size analysis. Attrition resistance of the calcined spray dry product was determined using the ARI method. Surface and core clay to alumina ratios were calculated using the EDS method described herein, with the average core clay to alumina ratio being 2.4. Various results are shown in Table 1.

Example 5

A slurry containing 45 wt % solid was prepared according to the following procedure: (a) adding 196.8 g of aluminum chlorohydrate (ACH) MicroDry (LOI: 50.6%; from Reheis Inc., Berkeley Heights, N.J.) to 483.9 g of deionized water, and mixing at 700 rpm for 10 minutes using a Yamato Model 2100 homogenizer (Yamato Scientific America Inc., Orangeburg, New York) to give a solution having pH of 3.70 at 24.4° C.; (b) adding 660.3 g of molecular sieve 71Q filtercake (LOI: 50.93%) to the solution from step (a) and mixing at 700 rpm for 10 minutes using the Yamato homogenizer Model 2100 used in step (a), the slurry thus obtained having a pH of 3.89 measured at 28.5° C.; (c) adding 459.1 g of ASP Ultrafine kaolin clay (LOI: 15.31%, Engelhard Corporation, Iselin, N.J.), while mixing at 700 rpm using the Yamato Model 2100 homogenizer, the resulting slurry having a pH of 3.88 at 24.7° C.; (d) passing the slurry from step (c) through a bead mill, Eiger mini bead mill model M250 (Eiger Machinery, Inc., Grayslake, Ill.) having a ceramic chamber and using a high density and high purity yttria-stabilized zirconia microbeads of 0.65 mm at 3500 rpm for a single pass, the slurry produced having a pH of 3.13 measured at 23° C. This slurry contained 44.85 wt % solids, of which 40% of the total weight of the solids were SAPO-34 sieve, 12% $Al_2O_3$, and 48% clay.

750 g of the slurry were then spray dried using a Yamato DL-41 spray dryer (Yamato Scientific America, Orangeburg, N.Y.). The spray dryer operated in a down spray mode using a 1 mm atomization nozzle. The spray drying conditions were: feed rate: 14-16 g/min; inlet temperature: 350° C.; atomization pressure: 1 bar; carrier gas (nitrogen) flow at 60% of full setting. Spray dried products were collected in a cyclone and calcined in a muffle furnace at 650° C. in air for 2 hours. The calcined samples were used for attrition and particle size analysis. Attrition resistance of the calcined spray dry product was determined using the ARI method. Surface and core clay to alumina ratios were calculated using the EDS method described herein, with the average core clay to alumina ratio being 2.4. Various results are shown in Table 1.

30.8° C.; (c) adding 351.7 g of ASP Ultrafine kaolin clay (Engelhard Corporation, Iselin, N.J.), while mixing at 700 rpm using the Yamato Model 2100 homogenizer, the resulting slurry having a pH of 3.65 at 30.1° C.; (d) passing the slurry from step (c) through a bead mill, Eiger mini bead mill model M250 (Eiger Machinery, Inc., Grayslake, Ill.) having a ceramic chamber and using a high density and high purity yttria-stabilized zirconia microbeads of 0.6 mm at 3000 rpm for a single pass, the slurry produced having a pH of 3.47 measured at 23° C. This slurry contained 44.81 wt % solids, of which 50% of the total solids weight was SAPO-34 sieve, 13.25% $Al_2O_3$, and 36.75% clay.

750 g of the slurry were then spray dried using a Yamato DL-41 spray dryer (Yamato Scientific America, Orangeburg, N.Y.). The spray dryer operated in a down spray mode using a 1 mm atomization nozzle. The spray drying conditions were: feed rate: 40 g/min; inlet temperature: 350° C.; atomization pressure: 1 bar; carrier gas (nitrogen) flow at 60% of full setting. Spray dried products were collected in a cyclone, and calcined in a muffle furnace at 650° C. in air for 2 hours. Calcined and uncalcined samples were used for attrition and particle size analysis using the ARI method. The results are shown in Table 2.

Example 7

A slurry containing 45 wt % solids was prepared according to the following procedure: (a) adding 265.8.5 g of aluminum chlorohydrate MicroDry (ACH, from Reheis Inc., Berkeley Heights, N.J.) to 712.9 g of deionized water and mixed at 700 rpm for 10 minutes using a Yamato Model 2100 homogenizer (Yamato Scientific America Inc., Orangeburg, N.Y.) to give a solution having pH of 3.65 at 27.3° C.; (b) adding 590.6 g of molecular sieve 74W to the solution from step (a) and mixing at 700 rpm for 10 minutes using the Yamato homogenizer Model 2100 used in step (a), the slurry thus obtained having a pH of 3.54 measured at 31.3° C.; (c) adding 230.6 g of ASP Ultrafine kaolin clay (Engelhard Corporation, Iselin, N.J.), while mixing at 700 rpm using the Yamato Model 2100 homogenizer, the resulting slurry having a pH of 3.58 at 30.7° C.; (d) passing the

TABLE 1

| Example | Binder:Sieve (wt:wt) | Slurry Solids (wt %) | Sieve Content (wt %) | Ageing (° C./16 hr) | ARI (%/hr) | Surface Clay:Alumina |
|---|---|---|---|---|---|---|
| 1 | 0.265 | 45.35 | 40 | — | 0.66 | 3.133 |
| 2 | 0.40 | 45.03 | 40 | 40 | 0.22 | 2.065 |
| 3 | 0.39 | 40.55 | 40 | — | 0.50 | 1.814 |
| 4 | 0.39 | 41.28 | 40 | 40 | 0.69 | — |
| 5 | 0.39 | 44.85 | 40 | — | 0.15 | 2.271 |

Example 6

A slurry containing 45 wt % solids was prepared according to the following procedure: (a) adding 221.5 g of aluminum chlorohydrate MicroDry (ACH, from Reheis Inc., Berkeley Heights, N.J.) to 734.6 g of deionized water, and mixing at 700 rpm for 10 minutes using a Yamato Model 2100 homogenizer (Yamato Scientific America Inc., Orangeburg, N.Y.) to give a solution having pH of 3.71 at 27° C.; (b) adding 492.29 g of molecular sieve 74W to the solution from step (a) and mixing at 700 rpm for 10 minutes using the Yamato homogenizer Model 2100 used in step (a), the slurry thus obtained having a pH of 3.60 measured at slurry from step (c) through a bead mill, Eiger mini bead mill model M250 (Eiger Machinery, Inc., Grayslake, Ill.) having a ceramic chamber and using a high density and high purity yttria-stabilized zirconia microbeads of 0.6 mm at 3000 rpm for a single pass, the slurry produced having a pH of 3.33 measured at 23° C. This slurry contained 44.61 wt % solids, of which 60% of the total weight of the solids were SAPO-34 sieve, 15.9% $Al_2O_3$, and 24.1% clay.

750 g of the slurry were then spray dried using a Yamato DL-41 spray dryer (Yamato Scientific America, Orangeburg, N.Y.). The spray dryer operated in a down spray mode using a 1 mm atomization nozzle. The spray drying conditions were: feed rate: 40 g/min; inlet temperature: 350° C.;

atomization pressure: 1 bar; carrier gas (nitrogen) flow at 60% of full setting. Spray dried products were collected in a cyclone, and calcined in a muffle furnace at 650° C. in air for 2 hours. Calcined and uncalcined samples were used for attrition and particle size analysis using the ARI method. The results are shown in Table 2.

Example 8

A slurry containing 45 wt % solids was prepared according to the following procedure: (a) adding 177.9 g of aluminum chlorohydrate MicroDry (ACH, from Reheis Inc., Berkeley Heights, N.J.) to 757.1 g of deionized water and mixing at 700 rpm for 10 minutes using a Yamato Model 2100 homogenizer (Yamato Scientific America Inc., Orangeburg, N.Y.) to give a solution having pH of 3.64 at 24.1° C.; (b) adding 393.7 g of molecular sieve 74W to the solution from step (a) and mixing at 700 rpm for 10 minutes using the Yamato homogenizer Model 2100 used in step (a), the slurry thus obtained having a pH of 3.60 measured at 26.8° C.; (c) adding 471.3 g of ASP Ultrafine kaolin clay (Engelhard Corporation, Iselin, N.J.), while mixing at 700 rpm using the Yamato Model 2100 homogenizer, the resulting slurry having a pH of 3.66 at 25° C.; (d) passing the slurry from step (c) through a bead mill, Eiger mini bead mill model M250 (Eiger Machinery, Inc., Grayslake, Ill.) having a ceramic chamber and using a high density and high purity yttria-stabilized zirconia microbeads of 0.6 mm at 3000 rpm for a single pass, the slurry produced having a pH of 3.23 measured at 23° C. This slurry contained 44.70 wt % solids, of which 40% of the total weight of the solids was SAPO-34 sieve, 10.6% $Al_2O_3$, and 49.4% clay.

750 g of the slurry was then spray dried using a Yamato DL-41 spray dryer (Yamato Scientific America, Orangeburg, N.Y.). The spray dryer operated in a down spray mode using a 1 mm atomization nozzle. The spray drying conditions were: feed rate: 40 g/min; inlet temperature: 350° C.; atomization pressure: 1 bar; carrier gas (nitrogen) flow at 60% of full setting. Spray dried products were collected in a cyclone and calcined in a muffle furnace at 650° C. in air for 2 hours. Calcined and uncalcined samples were used for attrition and particle size analysis using the ARI method. The results are shown in Table 2.

Example 9

A slurry containing 45 wt % solids was prepared according to the following procedure: (a) adding 201.4 g of aluminum chlorohydrate MicroDry (ACH, from Reheis Inc., Berkeley Heights, N.J.) to 746.9 g of deionized water and mixing at 700 rpm for 10 minutes using a Yamato Model 2100 homogenizer (Yamato Scientific America Inc., Orangeburg, N.Y.) to give a solution having pH of 3.62 at 24° C.; (b) adding 393.7 g of molecular sieve 74W to the solution from step (a) and mixing at 700 rpm for 10 minutes using the Yamato homogenizer Model 2100 used in step (a), the slurry thus obtained having a pH of 3.54 measured at 26.6° C.; (c) adding 458 g of ASP Ultrafine kaolin clay (Engelhard Corporation, Iselin, N.J.), while mixing at 700 rpm using the Yamato Model 2100 homogenizer, the resulting slurry having a pH of 3.64 at 25.3° C.; (d) passing the slurry from step (c) through a bead mill, Eiger mini bead mill model M250 (Eiger Machinery, Inc., Grayslake, Ill.) having a ceramic chamber and using a high density and high purity yttria-stabilized zirconia microbeads of 0.6 mm at 3000 rpm for a single pass, the slurry produced having a pH of 3.31 measured at 23° C. This slurry contained 44.79 wt % solids, of which 40% of the total weight of the solids was SAPO-34 sieve, 12% $Al_2O_3$, and 48% clay.

750 g of the slurry were then spray dried using a Yamato DL-41 spray dryer (Yamato Scientific America, Orangeburg, N.Y.). The spray dryer operated in a down spray mode using a 1 mm atomization nozzle. The spray drying conditions were: feed rate: 40 g/min; inlet temperature: 350° C.; atomization pressure: 1 bar; carrier gas (nitrogen) flow at 60% of full setting. Spray dried products were collected in a cyclone and calcined in a muffle furnace at 650° C. in air for 2 hours. Calcined and uncalcined samples were used for attrition and particle size analysis using the ARI method. The results are shown in Table 2.

Example 10

A slurry containing 45 wt % solid was prepared according to the following procedure: (a) adding 268.5 g of aluminum chlorohydrate MicroDry (ACH, from Reheis Inc., Berkeley Heights, N.J.) to 757.1 g of deionized water and mixing at 700 rpm for 10 minutes using a Yamato Model 2100 homogenizer (Yamato Scientific America Inc., Orangeburg, N.Y.) to give a solution having pH of 3.42 at 25.4° C.; (b) adding 393.7 g of molecular sieve 74W to the solution from step (a) and mixing at 700 rpm for 10 minutes using the Yamato homogenizer Model 2100 used in step (a), the slurry thus obtained having a pH of 3.35 measured at 27.6° C.; (c) adding 419.8 g of ASP Ultrafine kaolin clay (Engelhard Corporation, Iselin, N.J.), while mixing at 700 rpm using the Yamato Model 2100 homogenizer, the resulting slurry having a pH of 3.43 at 26.7° C.; (d) passing the slurry from step (c) through a bead mill, Eiger mini bead mill model M250 (Eiger Machinery, Inc., Grayslake, Ill.) having a ceramic chamber and using a high density and high purity yttria-stabilized zirconia microbeads of 0.6 mm at 3000 rpm for a single pass, the slurry produced having a pH of 3.19 measured at 23° C. This slurry contained 44.66 wt % solids, of which 40% of the total weight of the solids was SAPO-34 sieve, 16% $Al_2O_3$, and 44% clay.

750 g of the slurry were then spray dried using a Yamato DL-41 spray dryer (Yamato Scientific America, Orangeburg, N.Y.). The spray dryer operated in a down spray mode using a 1 mm atomization nozzle. The spray drying conditions were: feed rate: 40 g/min; inlet temperature: 350° C.; atomization pressure: 1 bar; carrier gas (nitrogen) flow at 60% of full setting. Spray dried products were collected in a cyclone and calcined in a muffle furnace at 650° C. in air for 2 hours. Calcined and uncalcined samples were used for attrition and particle size analysis using the ARI method. The results are shown in Table 2.

TABLE 2

| Example | Binder:Sieve (wt %:wt %) | Slurry Solids (wt %) | Sieve Content (wt %) | Calcined ARI (%/hr) | Uncalcined ARI (%/hr) |
|---|---|---|---|---|---|
| 6 | 0.265 | 44.81 | 50 | 0.19 | 0.06 |
| 7 | 0.265 | 44.61 | 60 | 0.27 | 0.06 |
| 8 | 0.265 | 44.70 | 40 | 0.31 | 0.13 |
| 9 | 0.300 | 44.79 | 40 | 0.17 | 0.04 |
| 10 | 0.400 | 44.66 | 40 | 0.13 | 0.06 |

Example 11

257.2 g of SAPO-34 molecular sieve filtercake were added to 255.5 g of deionized water, and mixed using a Yamato model D-4000 mixer (Yamato Scientific America Inc., Orangeburg, N.Y.) at 700 rpm for 10 minutes, then treated using a Silverson high shear mixer model L4RT-A (Silverson Machnies Inc., East Longmeadow, Mass.) at 6000 rpm for 3 minutes to give a thin slurry having a pH of 6.69 at 28° C. 77.2 g of Reheis MicroDry aluminum chlorohydrate (Reheis Chemical Inc., Berkeley Heights, N.J.) were added to the thin slurry, then mixed using the Yamato mixer at 700 RPM for 10 minutes followed by using the Silverson mixer at 6000 rpm for 3 minutes to give a slurry having a pH of 3.9 at 28° C. 210 g of Engelhard's USP kaolin clay (Engelhard Corporation, Iselin, N.J.) were then mixed in this slurry using the Yamato mixer at 700 rpm for 10 minutes followed by using the Silverson mixer at 6000 rpm for 3 minutes to give a slurry having a pH of 4.06 at 23° C. This slurry contained 45.26 wt % solids of which 40% of the total weight of the solids was SAPO-34 sieve, 10.6% alumina chlorohydrate derived alumina and 49.4% kaolin clay. The viscosity of the final slurry measured using a Brookfield LV viscometer, using a #3 spindle at 10 RPM, was 1440 centipoise at 23° C.

700 g of the slurry were spray dried using a Yamato DL-41 spray dryer operating in a down spray mode using a 1 mm atomization nozzle. The spray drying conditions were: feed rate: 40 g/min; inlet temperature: 350° C.; atomization pressure: 1 bar; carrier gas flow at 60% of full setting. Spray dried products were collected in a cyclone and calcined in a muffle furnace at 650° C. in air for 2 hours. The calcined samples were used for attrition and particle analysis. Attrition resistance of the spray dry product was determined using the ARI method. The apparent bulk density (ABD) was determined using the method described herein. The results are shown in Table 3.

Example 12

514.5 g of SAPO-34 molecular sieve filtercake were added to 511.1 g of deionized water, and mixed using a Yamato model D-4000 mixer (Yamato Scientific America Inc., Orangeburg, N.Y.) at 700 rpm for 10 minutes to give a having a pH of 6.67 at 22° C. 154.5 g of Reheis MicroDry aluminum chlorohydrate (Reheis Chemical Inc., Berkeley Heights, N.J.) were added to the slurry then mixed using the Yamato mixer at 700 rpm for 10 to give a slurry having a pH of 4.17 at 24° C. 420 g of Engelhard's USP kaolin clay (Engelhard Corporation, Iselin, N.J.) were added to this slurry and then mixed using the Yamato mixer at 700 rpm for 10 minutes to give a slurry having a pH of 4.19 at 24° C. This slurry was treated using an Eiger mini bead mill model M250 (Eiger Machinery, Inc., Grayslake, Ill.) having a ceramic chamber and using a high density and high purity yttria-stabilized zirconia microbeads of 0.6 mm at 3600 rpm for a single pass. The resultant slurry had a pH of 4.0 at 23° C., and contained 45.29 wt % solids, of which 40% of the total weight of the solids was SAPO-34 sieve, 10.6% alumina chlorohydrate derived alumina and 49.4% kaolin clay. The viscosity of the final slurry, which measured using a Brookfield LV viscometer with a #3 spindle at 10 RPM, was 850 centipoise at 23° C.

800 g of the slurry were spray dried using a Yamato DL-41 spray dryer operating in a down spray mode using a 1 mm atomization nozzle. The spray drying conditions were: feed rate: 40 g/min; inlet temperature: 350° C.; atomization pressure: 1 bar; carrier gas flow at 60% of full setting. Spray dried products were collected in a cyclone and calcined in a muffle furnace at 650° C. in air for 2 hours. The calcined samples were used for attrition and particle analysis. Attrition resistance of the spray dry product was determined using the ARI method. The ABD was determined using the method described herein. The results are shown in Table 3.

Example 13

350.6 g of SAPO-34 molecular sieve were added to 642.8 g of deionized water and mixed using a Yamato model D-4000 mixer (Yamato Scientific America Inc., Orangeburg, N.Y.) at 700 rpm for 10 minutes, then further mixed using a Silverson high shear mixer model L4RT-A (Silverson Machnies Inc., East Longmeadow, Mass.) at 6000 rpm for 3 minutes to give a thin slurry having a pH of 5.39 at 32° C. 231.7 g of Reheis MicroDry aluminum chlorohydrate (Reheis Chemical Inc., Berkeley Heights, N.J.) were added to the slurry mixture then mixed using the Yamato mixer at 700 rpm for 10 minutes followed by mixing using the Silverson mixer at 6000 rpm for 3 minutes to give a slurry having a pH of 3.18 at 35° C. 374.9 g of Engelhard's USP kaolin clay (Engelhard Corporation, Iselin, N.J.) were then added and mixed using the Yamato mixer at 700 rpm for 10 minutes followed by mixing using the Silverson mixer at 6000 rpm for 3 minutes to give a slurry having a pH of 3.63 at 23° C. This slurry contained 45 wt % solids, of which 40% of the total weight of the solids were SAPO-34 sieve, 15.9% alumina chlorohydrate derived alumina and 44.1% kaolin clay. The viscosity of the final slurry, which was measured using a Brookfield LV viscometer with a #3 spindle at 10 RPM, was 2320 centipoise at 23° C.

700 g of the slurry were spray dried using a Yamato DL-41 spray dryer operating in a down spray mode using a 1 mm atomization nozzle. The spray drying conditions were: feed rate: 40 g/min; inlet temperature: 350° C.; atomization pressure: 1 bar; carrier gas flow at 60% of full setting. Spray dried products were collected in a cyclone and calcined in a muffle furnace at 650° C. in air for 2 hours. The calcined samples were used for attrition and particle analysis. Attrition resistance of the spray dry product was determined using the AR1 method. The ABD was determined using the method described herein. The results are shown in Table 3.

Example 14

348.7 g of SAPO-34 molecular sieve were added to an aluminum chlorohydrate solution, prepared by adding 231.7 g of Reheis MicroDry aluminum chlorohydrate (Reheis Chemical Inc., Berkeley Heights, N.J.) to 162.4 g of deionized water, and mixed using a Yamato model D-4000 mixer (Yamato Scientific America Inc., Orangeburg, N.Y.) at 700 rpm for 10 minutes to give a slurry having a pH of 3.74 at 24° C. 374.9 g of Engelhard's USP kaolin clay (Engelhard Corporation, Iselin, N.J.) were added to the slurry and mixed using the Yamato mixer at 700 rpm for 10 to give a slurry having a pH of 3.61 at 24° C. This slurry was mixed using an Eiger mini bead mill model M250 (Eiger Machinery, Inc., Grayslake, Ill.) having a ceramic chamber and using a high density and high purity yttria-stabilized zirconia microbeads of 0.6 mm at 3000 rpm for a single pass. The resultant slurry had a pH of 3.69 at 23° C. The final slurry contained 45.18 wt % solids, of which 40% of the total weight of the solids was SAPO-34 sieve, 15.9% alumina chlorohydrate derived alumina and 44.1% kaolin clay. The viscosity of the slurry, which was measured using a Brookfield LV viscometer with a #3 spindle at 10 rpm, was 5890 centipoise at 23° C.

700 g of the slurry were spray dried using a Yamato DL-41 spray dryer operating in a down spray mode using a 1 mm atomization nozzle. The spray drying conditions were:

feed rate: 40 g/min; inlet temperature: 350° C.; atomization pressure: 1 bar; carrier gas flow at 60% of full setting. Spray dried products were collected in a cyclone and calcined in a muffle furnace at 650° C. in air for 2 hours. The calcined samples were used for attrition and particle analysis. Attrition resistance of the spray dry product was determined using the AR1 method. The ABD was determined using the method described herein. The results are shown in Table 3.

Example 15

350 g of SAPO-34 molecular sieve treated was added to an aluminum chlorohydrate solution, prepared by adding 231.7 g of Reheis MicroDry aluminum chlorohydrate (Reheis Chemical Inc., Berkeley Heights, N.J.) to 643.4 g of deionized water, and mixed using a Yamato model D-4000 mixer (Yamato Scientific America Inc., Orangeburg, N.Y.) at 700 rpm for 10 minutes to give a slurry having a pH of 3.55 at 28° C. 474.9 g of Engelhard's USP kaolin clay (Engelhard Corporation, Iselin, N.J.) were then added and mixed using the Yamato mixer at 700 rpm for 10 to give a slurry having a pH of 3.59 at 27° C. This slurry was mixed using an Eiger mini bead mill model M250 (Eiger Machinery, Inc., Grayslake, Ill.) having a ceramic chamber and using a high density and high purity yttria-stabilized zirconia microbeads of 0.6 mm at 3000 rpm for a single pass. The resultant slurry had a pH of 3.16 at 23 C. The final slurry contained 44.93 wt % solids, of which 40% of the total weight of the solids was SAPO-34 sieve, 15.9% alumina chlorohydrate derived alumina and 44.1% kaolin clay. The viscosity of the slurry, which was measured using a Brookfield LV viscometer with a #3 spindle at 10 rpm, was 900 centipoise at 23° C.

700 g of the slurry was spray dried using a Yamato DL-41 spray dryer operating in a down spray mode using a 1 mm atomization nozzle. The spray drying conditions were: feed rate: 40 g/min; inlet temperature: 350° C.; atomization pressure: 1 bar; carrier gas flow at 60% of full setting. Spray dried products were collected in a cyclone and calcined in a muffle furnace at 650° C. in air for 2 hours. The calcined samples were used for attrition and particle analysis. Attrition resistance of the spray dry product was determined using the ARI method. The ABD was determined using the method described herein. The results are shown in Table 3.

TABLE 3

| Example | Sieve Content (wt %) | Binder Content (wt %) | Slurry Solids (wt %) | Mixer Type | ABD | ARI (%/hr) |
|---------|---------------------|----------------------|---------------------|------------|------|------------|
| 11 | 40 | 10.6 | 45.26 | rotor-stator | 0.78 | 2.14 |
| 12 | 40 | 10.6 | 45.29 | bead mill | 0.80 | 0.56 |
| 13 | 40 | 15.9 | 45.00 | rotor-stator | 0.82 | 0.57 |
| 14 | 40 | 15.9 | 45.18 | bead mill | 0.87 | 0.24 |
| 15 | 40 | 15.9 | 44.93 | bead mill | 0.88 | 0.26 |

Having now fully described this invention, it will be appreciated by those skilled in the art that the invention can be performed within a wide range of parameters within what is claimed, without departing from the spirit and scope of the invention.

We claim:

1. A process for making olefin product from oxygenate, comprising the steps of:
    a) introducing a metalloaluminophosphate molecular sieve catalyst composition comprising metalloaluminophosphate molecular sieve crystals, clay and binder into a reaction system, wherein the catalyst has a core clay to alumina ratio of from 2.2:1 to 2.6:1, a surface clay to alumina ratio of from 1.7:1 to 3.1:1, and an attrition resistance index of not greater than 0.5 wt %/hr; and
    b) contacting the catalyst composition with oxygenate in the reaction system to form olefin product.

2. The process of claim 1, wherein the catalyst composition has a core clay to alumina ratio of from 2.3:1 to 2.5:1.

3. The process of claim 2, wherein the catalyst composition has a surface clay to alumina ratio of from 1.8:1 to 3:1.

4. The process of claim 3, wherein the catalyst composition has a surface clay to alumina ratio of from 1.9:1 to 2.9:1.

5. The process of claim 4, wherein the catalyst composition has a surface clay to alumina ratio of from 2:1 to 2.8:1.

6. The process of claim 1, wherein the catalyst composition has an attrition rate index of not greater than 0.4 wt %/hr.

7. The process of claim 6, wherein the catalyst composition has an attrition rate e index of not greater than 0.3 wt %/hr.

8. The process of claim 1, wherein the metalloaluminophosphate molecular sieve crystals are selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO47, SAPO-56, AlPO-5, AlPO-11, AlPO-18, AlPO-31, AlPO-34, AlPO-36, AlPO-37, AlPO-46, metal containing molecular sieves thereof, and mixtures thereof.

9. The process of claim 1, wherein the clay is a natural or synthetic clay.

10. The process of claim 1, wherein the binder is an inorganic oxide sol of alumina or silica.

11. The process of claim 1, wherein the catalyst composition is a spray dried catalyst composition.

12. The process of claim 1, wherein the catalyst composition is a calcined catalyst composition.

* * * * *